United States Patent
Causa et al.

(10) Patent No.: US 9,834,812 B2
(45) Date of Patent: Dec. 5, 2017

(54) PROBE KIT FOR DETECTING A SINGLE STRAND TARGET NUCLEOTIDE SEQUENCE

(71) Applicant: Fondazione Istituto Italiano Di Tecnologia, Genoa (IT)

(72) Inventors: Filippo Causa, Pompei (IT); Edmondo Battista, Nocera Inferiore (IT); Anna Aliberti, Siano (IT); Angela Maria Cusano, Caserta (IT); Paolo Netti, Naples (IT)

(73) Assignee: Fondazione Istituto Italiano Di Tecnologia, Genoa (IT)

( * ) Notice: Subject to any disclaimer, the term of this patent is extended or adjusted under 35 U.S.C. 154(b) by 177 days.

(21) Appl. No.: 14/655,276

(22) PCT Filed: Dec. 27, 2013

(86) PCT No.: PCT/IB2013/061377
§ 371 (c)(1),
(2) Date: Jun. 24, 2015

(87) PCT Pub. No.: WO2014/102748
PCT Pub. Date: Jul. 3, 2014

(65) Prior Publication Data
US 2016/0053308 A1 Feb. 25, 2016

(30) Foreign Application Priority Data
Dec. 27, 2012 (IT) .............. TO2012A1154

(51) Int. Cl.
C12Q 1/68 (2006.01)
C07H 21/00 (2006.01)
C12P 19/34 (2006.01)

(52) U.S. Cl.
CPC ........ *C12Q 1/6818* (2013.01); *C12Q 1/6816* (2013.01)

(58) Field of Classification Search
CPC ............ C12Q 1/68; C07H 21/00; C12P 19/34
See application file for complete search history.

(56) References Cited

U.S. PATENT DOCUMENTS

| | | | | |
|---|---|---|---|---|
| 4,818,682 A * | 4/1989 | Linnane | ............. | C07K 16/3046 435/4 |
| 2002/0165369 A1* | 11/2002 | Braman | .............. | C07F 15/0093 536/17.1 |

(Continued)

OTHER PUBLICATIONS

Ahern, H., The Scientist 9 (15) 20 (1995).*

(Continued)

*Primary Examiner* — Ethan C Whisenant
(74) *Attorney, Agent, or Firm* — Seed IP Law Group LLP

(57) ABSTRACT

There is disclosed a kit for detecting a single strand target nucleotide sequence comprising:
at least one first nucleic acid probe from 10 to 14 bases, to the 5' end of which at least one fluorophore is bound;
at least one second nucleic acid probe from 35 to 50 bases, comprising, from the 5' to the 3' end: a first segment having a nucleotide sequence complementary to the first nucleic acid probe, at least one quencher, and a second segment having a nucleotide sequence complementary to at least part of the target nucleotide sequence, wherein the following relation is met:

|Δ$G$ hybr.target3–probe2|>|Δ$G$ hybr.probe1–probe2|.

8 Claims, 7 Drawing Sheets

(56) References Cited

U.S. PATENT DOCUMENTS

| | | | | |
|---|---|---|---|---|
| 2003/0096351 | A1* | 5/2003 | Baker | C07K 14/47 435/69.1 |
| 2003/0108927 | A1* | 6/2003 | Leishman | A61K 31/198 435/6.16 |
| 2006/0024695 | A1* | 2/2006 | Li | C12Q 1/6851 435/5 |
| 2006/0292592 | A1* | 12/2006 | Happe | C12Q 1/6818 435/6.1 |
| 2008/0124705 | A1* | 5/2008 | Kramer | C12Q 1/6816 435/6.11 |
| 2009/0286249 | A1 | 11/2009 | Becker et al. | |

OTHER PUBLICATIONS

Atifi et al.,Long Oligonucleotide Arrays on Nylon for Large-Scale Gene Expression Analysis. Biotechniques 33 (3) 612(2002).*

Hakala et al., Time-Resolved Fluorescence Detection of Oligonucleotide Hybridization on a Single Microparticle: Covalent Immobilization of Oligonucleotides and Quantitation of a Model System. Bioconjugate Chemistry 8:232(1997).*

Lake et al., Molecular Logic Gates Connected through DNA Four-Way Junctions. Angewande Chem. Int. Ed. 49 :4459 (2010).*

Marras et al. Methods in Molecular Biology. vol. 335 ; p. 3 (2006) Edited by Didenko. Humana Press.*

Mo et al.A nanogold-quenched fluorescence duplex probe for homogeneous DNA detection based on strand displacement. Anal. Bioanal. Chem. 389 :493 (2007).*

Riahi et al. Supporting info for Analytical Chemistey 83 :6349 (2011).*

Zhang et al..Control of DNA Strand Displacement Kinetics Using Toehold Exchange JACS 131 :17303 (2009).*

Zhang et all., Label-free direct detection of MiRNAs with silicon nanowire biosensors. Biosensors and Bioelectronics 24 :2504 (2009).*

Li et al., "A new class of homogeneous nucleic acid probes based on specific displacement hybridization," *Nucleic Acids Research* *30*(2): e5, 2002, 9 pages.

Wang et al., "Molecular Engineering of DNA: Molecular Beacons," *Angew. Chem. Int. Ed. 48*: 856-870, 2009.

Gidwani et al., "Hybridization kinetics of double-stranded DNA probes for rapid molecular analysis," *Analyst 134*:1675-1681, 2009.

International Search Report and Written Opinion, dated Apr. 4, 2014, for International Application No. PCT/IB2013/061377, 13 pages.

Li et al., "Molecular beacons: An optimal multifunctional biological probe," *Biochemical and Biophysical Research Communications 373*:457-461, 2008.

Riahi et al., "Molecular Detection of Bacterial Pathogens Using Microparticle Enhanced Double-Stranded DNA Probes," *Analytical Chemistry 83*:6349-6354, 2011.

Wang et al., "Development of a Molecular Assay for Rapid Screening of Chemopreventive Compounds Targeting Nrf2," *JALA 13*:243-248, 2008.

* cited by examiner

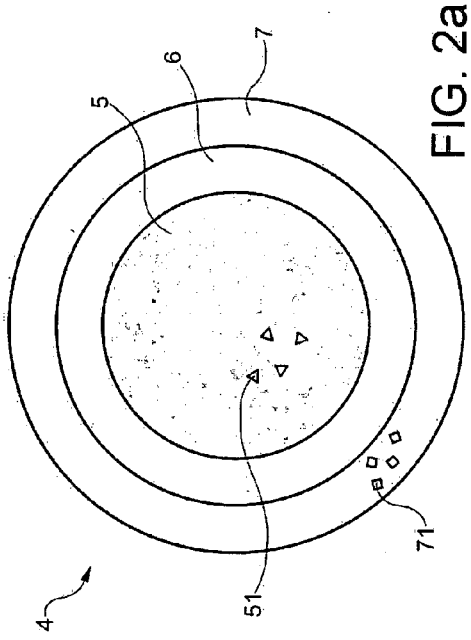
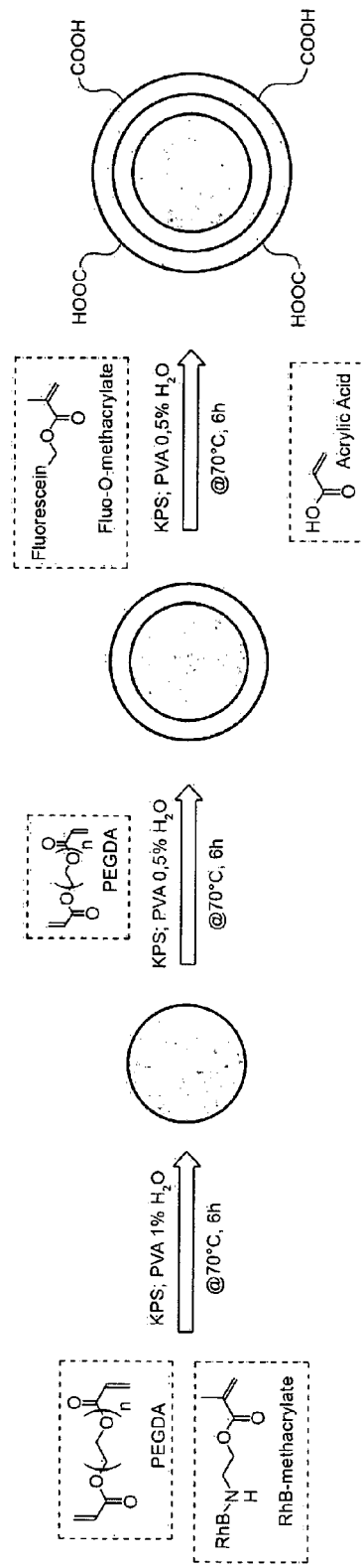
FIG. 2a
FIG. 2b

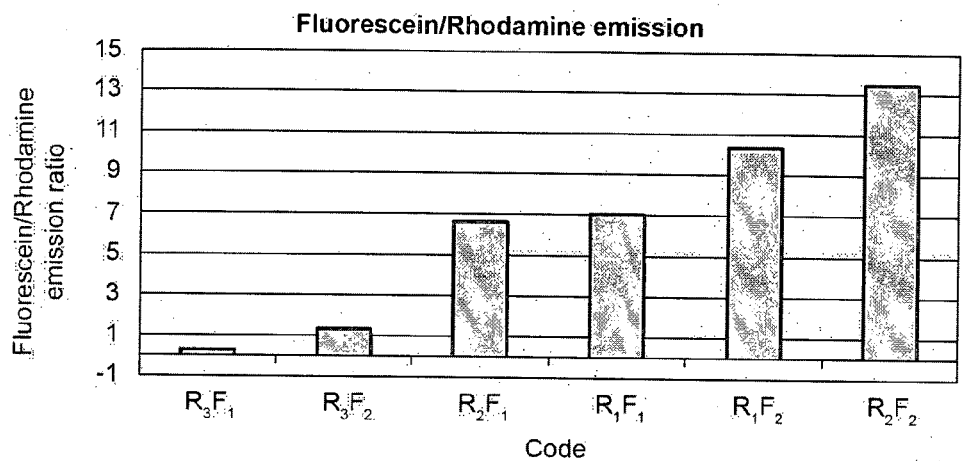
FIG. 7a
| Rhodamine [R-µM] | Fluorescein [F-µM] | Code |
|---|---|---|
| 0,1 | 0,1 | $R_3F_1$ |
| 0,1 | 0,2 | $R_3F_2$ |
| 0,01 | 0,1 | $R_2F_1$ |
| 0,005 | 0,1 | $R_1F_1$ |
| 0,005 | 0,2 | $R_1F_2$ |
| 0,01 | 0,2 | $R_2F_2$ |
FIG. 7b
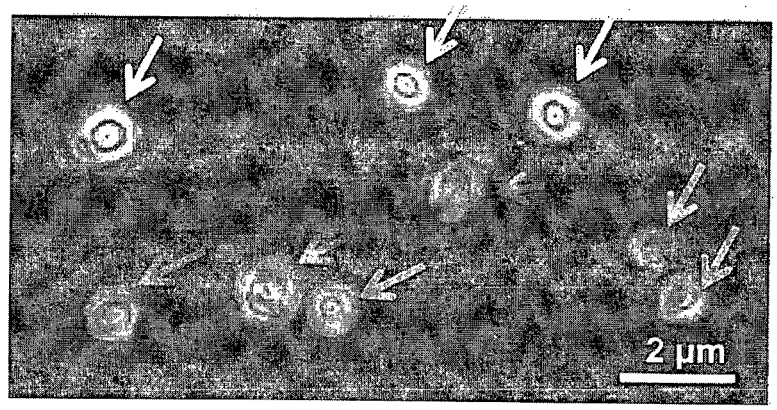
FIG. 7c

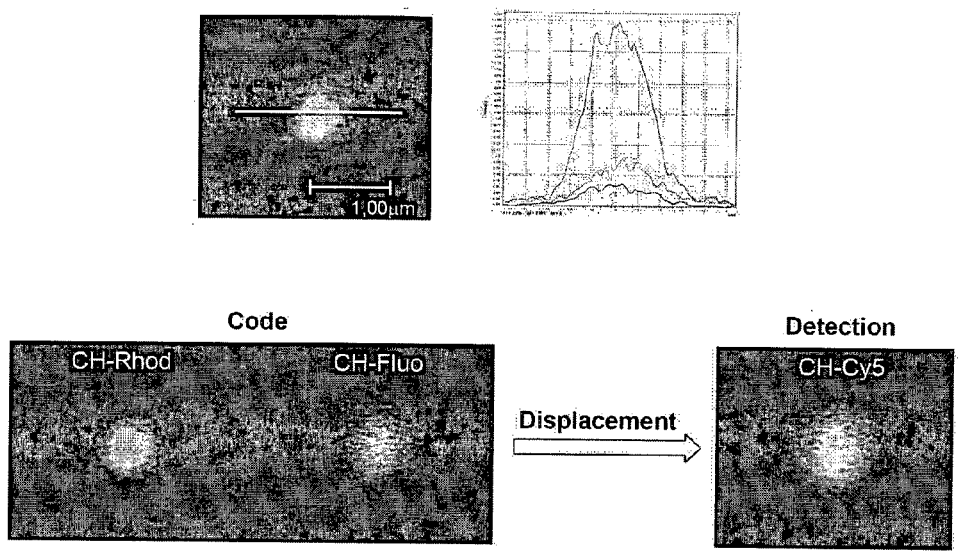
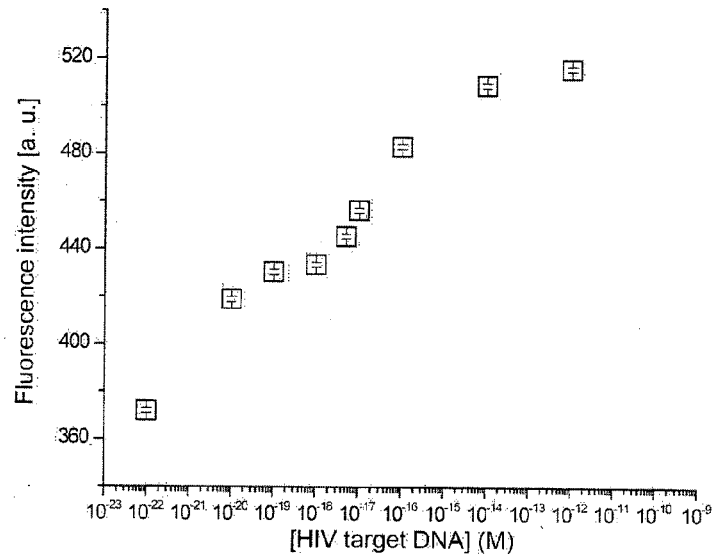
FIG. 8
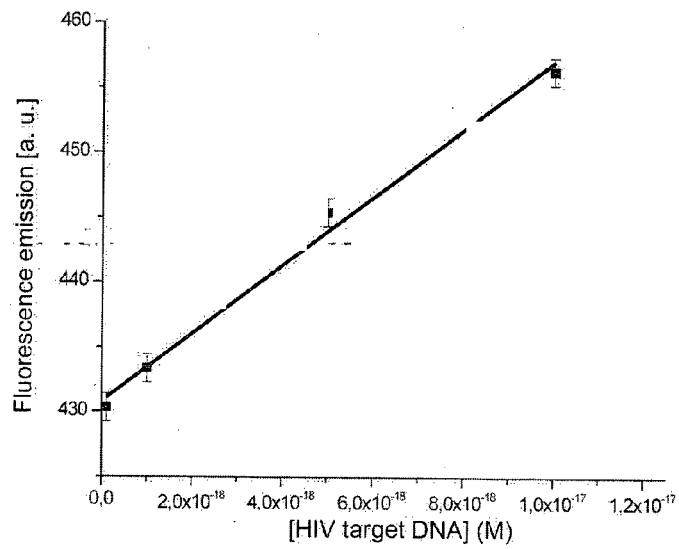
FIG. 9a
FIG. 9b

PROBE KIT FOR DETECTING A SINGLE STRAND TARGET NUCLEOTIDE SEQUENCE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 350050_401USPC_SEQUENCE_LISTING.txt. The text file is 7.2 KB, was created on Oct. 29, 2015, and is being submitted electronically via EFS-Web.

TECHNICAL FIELD

The present invention relates to a probe kit for detecting a single strand target nucleotide sequence.

STATE OF THE ART

Currently, assays for detecting single strand nucleic acids at low concentrations in multiplex are based on real-time PCR and Southern blotting methods, which require several amplification steps and different calibration systems, and also imply a considerable amount of time, money and labour. As an alternative, microarrays are known, which are however still manufactured by complex manufacturing procedures and are subsequently an expensive option.

In any case, amplification of the sample is required for all these assays in order to allow a sufficient detection sensitivity.

Some techniques based on the displacement of nucleic acids have been developed to increase the sensitivity of assays for the detection of single strand nucleic acids (Wang K. et al., Angew., Chem. Int. Ed. 2009, 48, 856-870; Li, Q. et al., Nucleic Acids Res. 2002 30, e5).

A first example of this strategy consists in molecular beacons (MB), single strand oligonucleotides with a stem-loop structure formed by 4 parts: a) a loop consisting of a region of 15-30 nucleotides complementary to the target sequence; b) a stem, i.e. a short duplex segment formed by 5-8 base pairs; c) a reporter which is generally bound to the 5' end and emits fluorescent light; d) a quencher bound to the 3' end, which absorbs the light radiation of the reporter.

During hybridization to the target sequence, the stem-loop structure of the molecular beacon undergoes a spontaneous fluorogenic conformational change. The molecular beacon design provides a mechanism for both molecular recognition and transduction of the hybridization events in one single step and thus dramatically accelerates the molecular detection process. In virtue of high sensitivity and high specificity, molecular beacons have been used for real-time quantitative determination of nucleic acids, for the construction of self-reporting oligonucleotide arrays, and even for analysis in vivo (Li Y. Zhou X. and Ye D. Biochem. Biophys. Res. Communications 2008, 373, 457-461).

A second example of the nucleic acid displacement strategy consists in the double-stranded assay, in which a nucleotide sequence containing a fluorophore labelled on the 5' end is designed to be complementary to the nucleotide sequence of interest. To allow homogeneous detection of the target, a complementary sequence is designed with respect to the fluorophore probe but with a shorter length and its 3' end is labelled with a quencher. In the absence of the target, the fluorophore and quencher probes are in close proximity diminishing the fluorescence signal. With the target, the quencher probe is replaced due to the thermodynamically driven binding event between the fluorophore probe and the target. Therefore, the fluorophore is separated from the quencher and is able to fluoresce.

Compared to other homogeneous assays for nucleic acids, such as those employing molecular beacons, advantages of dsDNA probes include the possibility of adjusting the quencher-to-fluorophore ratio for noise minimization and the flexibility of modifying the lengths of the quencher sequence and the sticky end for improving the specificity, selectivity and kinetics of the assay.

However, most dsDNA assays require target amplification, such as PCR, to obtain a sufficient sensitivity (Riahi R. et al., Anal. Chem. 2011, 83 6349-6354).

Furthermore, double-strand DNA assays have further important drawbacks.

In particular, as regards the length of the nucleic acids to analyse, these assays have generally been shown to be effective only for lengths longer than 50 bases.

Furthermore, it is difficult to control and modulate the displacement process on the basis of the gain of free energy of the considered systems.

Moreover, they are expensive and have a limited stability and shelf life.

Finally, they often display a high aspecific signal when used in complex biological samples, for example blood or plasma, due to aspecific interactions with several proteins. In view of this, a sample separation step is generally required before the actual detection step.

OBJECT OF THE INVENTION

It is therefore an object of the present invention to develop a kit for detecting a single strand target nucleotide sequence allowing to overcome at least one of the above said problems in a simple, effective and cost-effective manner.

The above said object is achieved by the present invention as it relates to a kit for detecting a single strand target nucleotide sequence as defined in claim 1.

BRIEF DESCRIPTION OF THE DRAWINGS

For a better understanding of the present invention a preferred embodiment is disclosed hereinafter by way of non-limitative example and with reference to the accompanying drawings, in which:

FIG. 2A is a diagrammatic representation of a microparticle according to the present invention;

FIG. 2B is a diagram of the process for preparing a microparticle according to the present invention;

FIGS. 7A and 7B show the fluorescence codes of 6 microgels (i.e. a set of microparticles) obtained using different concentrations of first and second fluorophore respectively in the first and third layer of microparticles shown in FIG. 2A;

FIG. 7C shows an image of three microgels with different codes obtained using different concentrations of first and second fluorophore respectively in the first and, third layer of microparticles shown in FIG. 2A;

FIG. 8 shows images obtained by CLSM and intensities measured along the axis of the microgel. The channel for the code analysis and detection of the displacement are shown in the lower part;

FIG. 9A is a diagram showing the fluorescence recovery on the surface of the microgels as a function of the different concentrations of the target sequence (HIV);

FIG. 9B is a diagram showing the linear regression of the fluorescence emissions as a function of the concentration of a target sequence for the computation of the detection limit (HIV);

DETAILED DESCRIPTION

Figure 1:
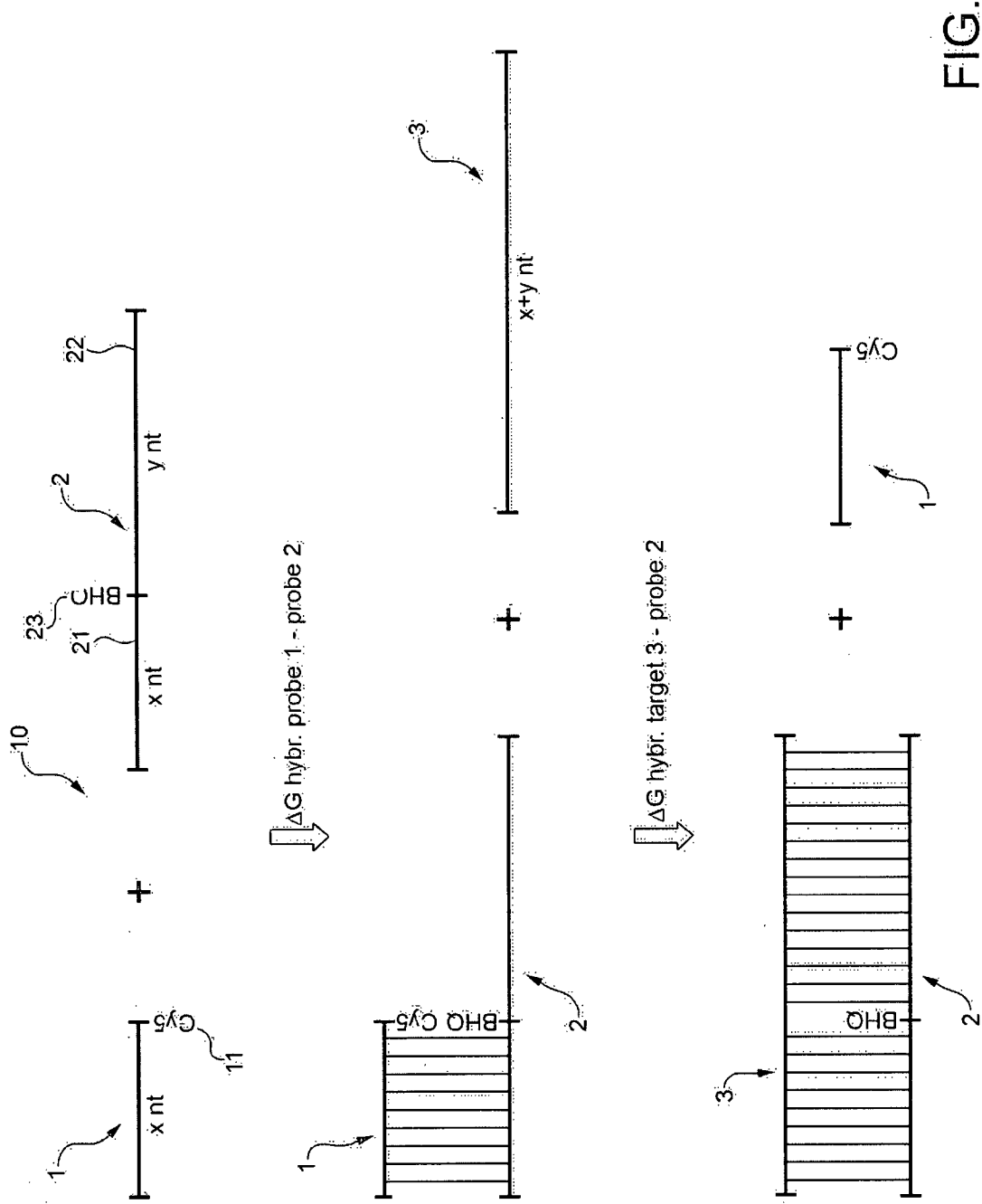
FIG. 1 is a diagrammatic representation of the probe kit according to the present invention and of the operation thereof.

Kit 10 per for detecting a single strand target nucleotide sequence 3 according to the present invention comprises at least one first nucleic acid probe 1 and at least one second nucleic acid probe 2.

Probe 1 has a length from 10 to 14 bases, preferably from 11 to 13 bases, and has at least one fluorophore 11 bound at the 5' end.

Probe 2 has a length from 35 to 50 bases and comprises, from the 5' end to the 3' end:

a first segment 21 of nucleotide sequence complementary to probe 1,
  at least one quencher 23, and
    a second segment 22 of nucleotide sequence complementary to at least part of the target nucleotide sequence 3.

In the case shown, both probe 1 and probe 2 are made of DNA.

Fluorophore 11 bound to the 5' end of probe 1 is preferably selected from the group consisting of FAM, TET, JOE, HEX, Oregon Green®, TAMRA, ROX, Cy3, Cy3.5, Cy5, Cy5.5, CAL Red™, Red 640, Cy5, and Cy5.5.

Quencher 23 of probe 2 is preferably selected from the group consisting of DDQ-I, Dabcyl, Eclipse, Iowa Black FQ, BHQ-1, QSY-7, BHQ-2, DDQ-II, Iowa Black RQ, QSY-21, and BHQ-3 and is compatible with fluorophore 11 bound to the 5' end of probe 1.

Advantageously, probe 1 and probe 2, are designed so that the following relation is met:

$|\Delta G$ hybr.target3–probe2$|>|\Delta G$ hybr.probe1–probe2$|$, where:

$\Delta G$ hybr.target3–probe2 is the free energy of duplex formation between target nucleotide sequence 3 and second nucleic acid probe 2, and $\Delta G$ hybr.probe1–probe2 is the free energy of duplex formation between the first nucleic acid probe 1 and the second nucleic acid probe 2.

More preferably, probe 1 and probe 2 are designed so that

10 Kcal/mol$>|\Delta G$ hybr.target3–probe2$|-|\Delta G$ hybr. probe1–probe2$|>$50 Kcal/mol.

When target nucleotide sequence 3 is DNA, probe 1 and probe 2 are even more preferably designed so that 35 Kcal/mol$>|\Delta G$ hybr.target3–probe2$|-|\Delta G$ hybr. probe1–probe2$|>$45 Kcal/mol.

When target nucleotide sequence 3 is miRNA, probe 1 and probe 2 are even more preferably designed so that 10 Kcal/mol$>|\Delta G$ hybr.target3–probe2$|-|\Delta G$ hybr.probe1–probe2$|>$25 Kcal/mol.

In the case at issue, the Oligocalc software (Nucl. Acids Res. (2007) 35 (suppl2):W43-W46) was used to compute the $\Delta G$ values.

As most of the software packages commercially available for the design of oligonucleotides, this software uses the value of $\Delta G$ as a measure of the affinity between two nucleotide sequences, where the affinity represents the measure of the thermodynamic stability of the duplex formed by the two single strand oligonucleotides.

The transition from one state (2 single strands) to another state (duplex) results in an energy variation in the system.

$\Delta G$ is the variation in Gibbs free energy (unit: kcal/mole) and represents the net exchange in energy between the system and its environment and is described by the following equation $$\Delta G = \Delta H - T \cdot \Delta S$$

where $\Delta H$ (enthalpy) represents the total energy exchange between the system and the surrounding environment (kcal/mole) and $\Delta S$ (entropy) represents the energy used by the system to organise itself (cal/K·mol). In general, spontaneous system favours a more random system rather than a less random one. Finally, T represents the absolute temperature of the system in Kelvin degrees (Celsius+273.15).

The description of $\Delta G$ indicates that this amount depends on the temperature. In the case at issue, reactions have been performed at room temperature. Therefore, $\Delta G$ has been computed for T=25° C. (298.15 Kelvin).

At a given temperature a positive $\Delta G$ value indicates that the system tends to evolve towards single strand reagents (non spontaneous). A negative value of $\Delta G$ indicates, instead, that the system tends to evolve towards a duplex product (spontaneous).

For greater clarity and simplicity, in the present patent application, the values of $\Delta G$ are indicated as an absolute value.

Target nucleotide sequence 3 preferably has a length from 15 to 100 bases, even more preferably from 20 to 40 bases.

Kit 10 allows to detect target nucleotide sequences 3 in a range of concentrations from $1 \cdot 10^{-11}$ M to $1 \cdot 10^{-22}$ M, i.e. in a very broad range. In particular, kit 10 allows to detect target nucleotide sequences 3 at concentrations from $1 \cdot 10^{-17}$ M to $1 \cdot 10^{-19}$ M, i.e. a very low concentrations. With reference to FIG. 1, probe 1, probe 2 and target nucleotide sequence 3 are shown. In the case at issue, probe 1 is x bases long (for example, 12 bases) and has a Cy5 molecule bound at the 5' end. Probe 2 is x+y bases long (for example, 39 bases) and comprises, from the 5' to the 3' end, a first segment 21 which is x bases long (for example, 12 bases long) and complementary to probe 1, a quencher 23 (BHQ), and a second segment 22 which is y bases long (for example, 27 bases long) and complementary to at least part of target nucleotide sequence 3. Target nucleotide sequence 3 is x+y bases long (for example, 39 bases long).

In the presence of probe 1 and probe 2, these form a duplex having formation free energy ΔG hybr.probe1-probe2. In this situation, quencher 23 BHQ quenches the signal emitted by fluorophore 11 Cy5 and there is no fluorescence emission.

When target nucleotide sequence 3 is added to probes 1 and 2, the reaction equilibrium shifts towards the formation of the duplex between target nucleotide sequence 3 and probe 2, because |ΔG hybr.target3−probe2|>|ΔG hybr.probe1−probe2|. The displacement of quencher 23 BHQ from fluorophore 11 Cy5 caused by the displacement of probe 1 from probe 2 results in the emission of fluorescence.

Probe 1 and probe 2 are designed on the basis of target nucleotide sequence 3 and their thermodynamic affinity is modulated so that the affinity of probe 2 for target nucleotide sequence 3 is higher than the affinity of the initial duplex between probe 1 and probe 2. The difference in free energy |ΔG hybr.target3−probe2|−|ΔG hybr.probe1−probe2| and the length of probe 1 are selected so as to optimize the displacement of probe 1 and the formation of the duplex between probe 2 and target nucleotide sequence 3.

Figure 3:
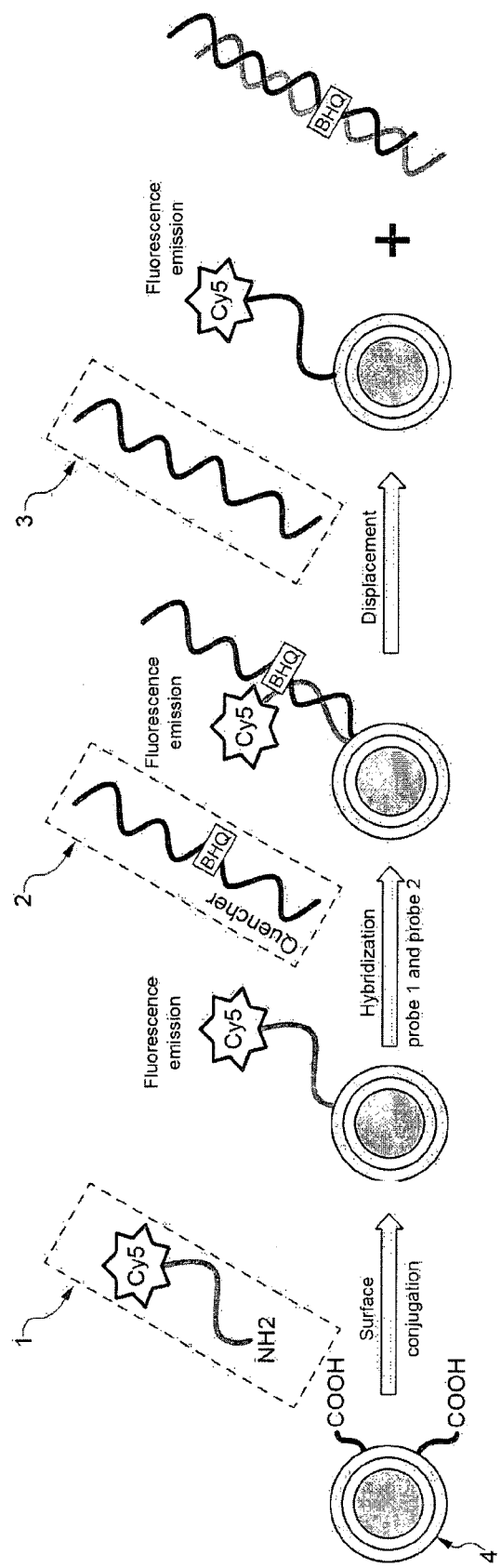
FIG. 3 is a diagrammatic representation of the conjugation of a probe kit and a microparticle according to the present invention.

With reference to FIG. 3, in a preferred embodiment, kit 10 also comprises at least one microparticle 4 covalently bound to the 3' end of probe 1, preferably by means of an amide bond. Even more preferably, the bond between microparticle 4 and probe 1 is obtained by means of an appropriate amino-linker on probe 1.

With reference to FIG. 2A, multilayer particle 4 according to the present invention comprises:
  at least one first layer 5 comprising a first fluorophore 51,
  at least one second layer 6 in contact with first layer 5, and
  at least one third layer 7 in contact with second layer 6 and comprising a second fluorophore 71.

First fluorophore 51 and second fluorophore 71 are different, first layer 5 and third layer 7 are not in contact with one another.

First fluorophore 51 and second fluorophore 71 can be selected from the group consisting of rhodamine, fluorescein, Cy2, Oregon Green, Alexa (488, 532, 546, 555) and others as long as the emission wave length do not overlap.

Preferably, multilayer microparticle 4 also comprises:
  at least one fourth layer 8 in contact with third layer 7, and
  a least one fifth layer 9 in contact with fourth layer 8 and comprises a third fluorophore 91.

Third fluorophore 91 is different from second fluorophore 71 and from first fluorophore 51, and third layer 7 and fifth layer 9 are not in contact with one another.

The third fluorophore can be selected from the group consisting of rhodamine, fluorescein, Cy2, Oregon Green, Alexa (488, 532, 546, 555) and others as long as the emission wavelengths do not overlap with the wavelengths of first and second fluorophore 51, 71.

Multilayer microparticle 4 preferably has a size from 0.5 μm to 2 μm.

Each layer of multilayer microparticle 4 preferably comprises esters and amides of acrylic acid or of methacrylic acid or vinyls or allyls, which are optionally substituted.

By "esters and amides of acrylic acid or of methacrylic acid or vinyls or allyls, which are optionally substituted" there is also intended compounds equivalent thereto. This definition also includes difunctional polymers used as cross-linkers such as, for example, bisacrylammide, polyethyl-enoxide-acrylate/-methacrylate etc.

Fluorophores 51, 71, 91 included in layers 5, 7, 9 may be used in the form of acrylates or methacrylates or vinyls or allyls with other chemical groups which allow the chemical bond to the polymer network of layers 5, 7, 9.

FIG. 2B shows the process for the preparation of a specific multilayer microparticle 4. In a first step, a first layer 5 of polyethylene glycol dimethacrylate (PEGDA, 500 MW) and rhodamine B acrylate monomers is produced by free-radical precipitation polymerization. In a following step, a second layer 6 of polyethylene glycol dimethacrylate is produced around first layer 5 by seeded polymerization. In a following step, a third layer 7 of acrylic acid and fluorescein is produced around second layer 6 by seeded polymerization. Different groups of microparticles with different fluorescence codes can be obtained by using different concentration ratios between rhodamine and fluorescein.

EXAMPLES

Example 1—Synthesis of Microparticles

With reference to FIG. 2B an example of synthesis of a specific type of microparticles is disclosed in detail.

Synthesis of First Layer 5.

Microgels of polyethylene glycol dimethacrylate have been prepared by free-radical precipitation polymerization, using a concentration of total monomers of 1% (w/v). Polymerization has been performed in a 100 ml three-neck flask with round bottom, in which a filtered aqueous solution of monomers and 1% (w/v) polyvinyl alcohol (PVA) as surfactant have been added. This solution was heated to ~65° C. while being purged with $N_2$ gas and stirred vigorously for ~1 h. Then the reaction was immediately initiated by injection of a potassium persulfate (KPS) aqueous solution (to make a final KPS concentration of 0.06% w/v). The solution turned turbid, indicating successful initiation. Methacryloxy thiocarbonyl rhodamine B, dissolved in dimethyl sulfoxide (0.1 ml) and diluted with water (1.9 ml), was then added to the stirred mixture at a final concentration ranging from 0.005 to 0.3 mM to obtain different dye amounts. The solution was allowed to heat and stir for an additional 7 h while being purged with $N_2$ gas. The microgels were dialyzed for 2 days against distilled water, purified several times by centrifuging for 15 minutes at 12000 rpm and resuspending in deionised water to remove unreacted monomers, oligomers and surfactants and stored at 4° C. until further use.

Synthesis of Second Layer 6.

The rhodamine-labelled microgel was resuspended in deionised water to a concentration of 10 mg/ml. These microgels were then used as seed particles, upon which a PEGDMA cross-linked layer was added. A solution of rhodamine-labelled core microgels (100 mg, 10 ml) in deionised water (25 ml) was heated to 65° C. under a gentle stream of $N_2$. Separately, PEGDMA (240 mg) was dissolved in water (10 ml), purged with $N_2$ at room temperature and then slowly added to the heated core solution. After the temperature remained stable at 65° C. for ~1 h, 2 ml of aqueous solution of KPS (final concentration of 0.03% w/v) was added to initiate the polymerization. The reaction was allowed to proceed, for 6 h. The microgels were purified several times by centrifugation (15 minutes at 9000 rpm) and resuspended in deionised water.

Synthesis of Third Layer 6.

A solution of two layer (core-shell) microgels (10 ml, [C]=10 mg/ml) in deionised water (25 ml) was heated to 65° C., followed by the slow addition of 10 ml of aqueous monomer solution containing PEGDMA (240 mg) and acrylic acid (125 mg). After the temperature remained stable at 65° C. for ~1 h, 2 ml of aqueous solution of KPS (final concentration of 0.03% w/v) was added to initiate the polymerization. Fluorescein O-methacrylate diluted in water (2 ml), was then added to the stirred mixture at a final concentration ranging from 0.05 to 0.2 mM to obtain different dye amounts. The reaction was allowed to proceed for 6 h. The microgels were dialyzed for 5 days, purified several times by centrifugation (for 15 minutes at 6500 rpm) and resuspended in deionised water to remove unreacted monomers, oligomers and surfactants, then stored at 4° C. prior to use until further use.

Microgel Surface Functionalisation.

1 mg of encoded microgels was dissolved in 250 µl of coupling buffer, 100 mM MES pH 4.8, and kept at 4° C. with occasional vortexing for at least 1 h to disperse the colloidal particles. 1-ethyl-3-(3-dimethylaminopropyl)carbodiimide (EDC) (500 mM, final concentration, dissolved in the coupling buffer that was freshly prepared, just before use) was added to this suspension, followed by the addition of 1200 pmol of probe 1. The total reaction volume was approximately 500 µl. The reaction mixture was carried on in dark and left at 4° C. in a shaker over night. The conjugate between probe 1 and multilayer microparticle 4 was precipitated down by centrifugation at 6000 rpm for 15 min at room temperature. The supernatant was removed carefully with a pipette and the precipitant was resuspended in 1 ml Of Tris HCl, pH 8 buffer by agitating with a pipette tip and brief vortexing. This washing step was repeated three more times.

Example 2—Microparticles with Different Ratios Between First Fluorophore 51 and Second Fluorophore 71

Polyethylene glycol (PEG) microgels were produced (particle size of about 1 µm). The outer layer of these microparticles 4 was functionalised with carboxylic groups. Two concentrations of fluorescein 71 (0.1 µm and 0.2 µm) were used for third layer 7, and three different concentrations of rhodamine 51 (0.1 µm, 0.01 µm e 0.005 µm) were used for first layer 5. Six microgels were distinguished by means of a spectrofluorometer, on the basis of combinations of different concentrations of rhodamine 51 and fluorescein 71 in the production solution of multilayer microparticles 4 (FIGS. 7A and 7B).

As may be noted in FIG. 7C, the approach for multilayer microparticle 4 production allows to define an univocal code on the particles in virtue of the fact that fluorophores 51, 71 are confined in space. In particular, confocal microscope images were obtained of three microgels with different codes obtained by means of different concentration ratios between rhodamine 51 and fluorescein 71 respectively in first layer 5 and in third layer 7 of multilayer microparticle 4.

Figure 4:
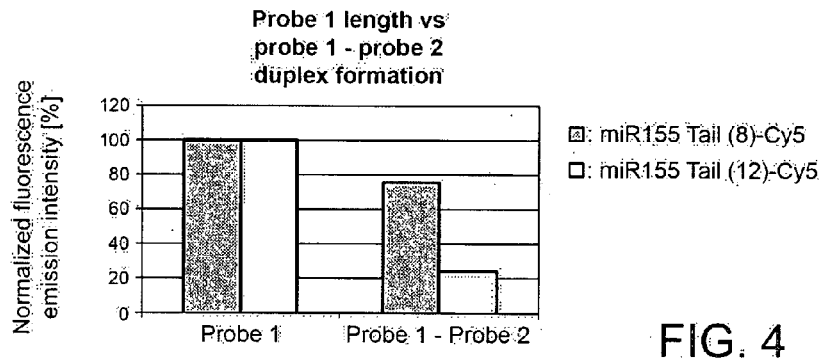
FIG. 4 is a diagram showing the effects of the length of a first probe on the formation of the duplex between the first and the second probe of the probe kit of FIG. 1.

Example 3—Effect of the Length of Probe 1 on the Formation of the Duplex Between Probe 1 and Probe 2 of the Probe Kit According to the Invention FIG. 4 shows how the length of probe 1 influences the formation of the duplex between probe 1 and probe 2 of probe kit 10 according to the invention. In particular, the results for a probe 1 of 8 bases and a probe 1 of 12 bases are shown. 0.1 µM solutions of probe 1 (8 and 12 bases long) and probe 2 were reacted for 12 hours and fluorescence emission was evaluated. From the data of FIG. 4 it is apparent that the bond between probe 1 (8 bases long) and probe 2 is poorly stable as can be seen from the measurements of fluorescence relating to the formation of the duplex. In this case a very low loss in the percentage of fluorescence is registered. Instead, the duplex between probe 1 (12 bases) and probe 2 results more stable as confirmed by a greater percent loss of fluorescence emission of the complex probe 1-probe 2 if compared to sole reference probe 1.

Example 4—Computation of ΔG for Probe Systems for HIV, HCV, SARS and miRNA

The values of ΔG have been computed by means of the Oligocalc software.

TABLE 1

| Probe name | Sequence | Length | ΔG (Kcal/mol) |
|---|---|---|---|
| HIV probes (on the basis of Genbank sequence: AF033819.3 positions 6520-6559) | | | |
| HIV first probe (tail-Cy5) | 5' Cy5 ACT GCT GTT AAA C6 NH$_2$-3' | 12 | $|\Delta G_{hybr.probe1-probe2}|$ 11.2 |
| HIV second probe (quencher) | 5' TTT AAC AGC AG BHQ TGA GTT GAT ACT ACT GGC CTA ATT CCA 3' (SEQ ID NO: 22) | 39 | $|\Delta G_{hybr.target3-probe2}|$ 50.9 |
| HIV target nucl. seq. (target) | 5' TGG AAT TAG GCC AGT AGT ATC AAC TCA ACT GCT GTT AAA 3' (SEQ ID NO: 3) | 39 | |

$|\Delta G_{hybr.target3-probe2}|$ −
$|\Delta G_{hybr.probe1-probe2}|$
39.7

TABLE 1-continued

| Probe name | Sequence | Length | ΔG (Kcal/mol) |
|---|---|---|---|
| HCV probes (on the basis of Genbank sequence: M67463.1 positions 160-195) | | | |
| HCV first probe (tail-Cy5) | 5' Cy5 TTC CGG TGT ACT-C6 NH2-3' (SEQ ID NO: 4) | 12 | $\|\Delta G_{hybr.probe1-probe2}\|$ 13.3 |
| HCV second probe (quencher) | 5'-AGT ACA CCG GABHQ TTG CCA GGA CGA CCG GGT CCT TT-3' (SEQ ID NO: 23) | 35 | $\|\Delta G_{hybr.target3-probe2}\|$ 53.7 |
| HCV target nucl. seq. (target) | 5'- AAA GGA CCC GGT CGT CCT GGC AAT TCC GGT GTA CT -3' (SEQ ID NO: 6) | 35 | |
| | | | $\|\Delta G_{hybr.target3-probe2}\| - \|\Delta G_{hybr.probe1-probe2}\|$ 40.4 |
| SARS probes (on the basis of human coronavirus sequence 229E, whole genome, Genbank: AF304460 positions 16710-16747) | | | |
| SARS first probe (tail-Cy5) | 5' Cy5 GGC TCC AGT ATA -C6 NH2-3' (SEQ ID NO: 7) | 12 | $\|\Delta G_{hybr.probe1-probe2}\|$ 11.9 |
| SARS second probe (quencher) | 5'- TAT ACT GGA GCBHQ ATT GTC TAC CTG AAC ACT ACC GCG T -3' (SEQ ID NO: 24) | 37 | $\|\Delta G_{hybr.target3-probe2}\|$ 52.4 |
| SARS target nucl. seq. (target) | 5'- ACG CGG TAG TGT TCA GGT AGA CAA TGG CTC CAG TAT A -3' (SEQ ID NO: 9) | 37 | |
| | | | $\|\Delta G_{hybr.target3-probe2}\| - \|\Delta G_{hybr.probe1-probe2}\|$ 40.5 |
| Hsa_miRNA 155 (from www.mirbase.org) | | | |
| miR155 first probe (tail(12)-Cy5) | 5'- Cy5 CGT GAT AGG GGT NH2-3' (SEQ ID NO: 10) | 12 | $\|\Delta G_{hybr.probe1-probe2}\|$ 13.6 |
| miR155 second probe (quencher 12) | 5'-ACC CCT ATC ACBHQ ATT AGC ATT AA-3' (SEQ ID NO: 25) | 23 | $\|\Delta G_{hybr.probe1-probe2}\|$ 6.1 |
| miR155 first probe (tail(8)-Cy5) | 5'-Cy5 AT AGG GGT NH2-3' (SEQ ID NO: 12) | 9 | |
| miR155 second probe (quencher 8) | 5'-ACC CCT ABHQ CACBHQ ATT AGC ATT AA-3' (SEQ ID NO: 26) | 23 | |
| miR155 target nucl. seq. (target) | 5'-TTAATGCTAATCGTGATAGGGGT-3' (SEQ ID NO: 14) | 23 | |
| miR155 target nucl. seq. (target) | 5'-UUAAUGCUAAUCGUGAUAGGGGU-3' (SEQ ID NO: 15) | 23 | $\|\Delta G_{hybr.target3-probe2}\|$ 28 |
| | | | $\|\Delta G_{hybr.target3-probe2}\| - \|\Delta G_{hybr.probe1-probe2}\|$ (12) 14.4 $\|\Delta G_{hybr.target3-probe2}\| - \|\Delta G_{hybr.probe1-probe2}\|$ (8) 21.9 |

TABLE 1-continued

| Probe name | Sequence | Length | ΔG (Kcal/mol) |
|---|---|---|---|
| Hsa_miRNA 21 (from www.mirbase.org) | | | |
| miR21 first probe (tail-Cy5) | 5'-Cy5 GACTGATGTTGA NH$_2$-3' (SEQ ID NO: 16) | 12 | $\Delta G_{hybr.probe1-probe2}$ \| 11.2 |
| miR21 second probe (quencher 12) | 5'-TCAACATCAGTBHQTGATAAGCTA-3' (SEQ ID NO: 27) | 22 | $\|\Delta G_{hybr.target3-probe2}\|$ 25.1 |
| miR21 target nucl. seq. (target) | 5'-UAGCUUAUCAGACUGAUGUUGA-3' (SEQ ID NO: 18) | 22 | |
| | | | $\|\Delta G_{hybr.target3-probe2}\|$ − $\|\Delta G_{hybr.probe1-probe2}\|$ 13.9 |

Example 5—Homogeneous Phase Assay with Short Probes

An experiment was performed with a probe kit, to which no microparticles were conjugated, i.e. in homogeneous phase.

40 pmoles of probe 1 were mixed with 40 pmoles of probe 2 in Tris HCl, pH 8. Quenched samples were used as reference in order to evaluate the displacement efficiency. The specificity of double strand probes was evaluated by using scrambled or non specific sequences. Each sample was loaded onto a 96-well microplate and the fluorescence emission intensity was measured in 2300 EnSpire multilabel reader (Perkin-Elmer, Waltham, Mass.) by setting the λex=633 and λem=654.

The indicated experimental uncertainties represent the standard deviation of three replicates.

Figure 5:
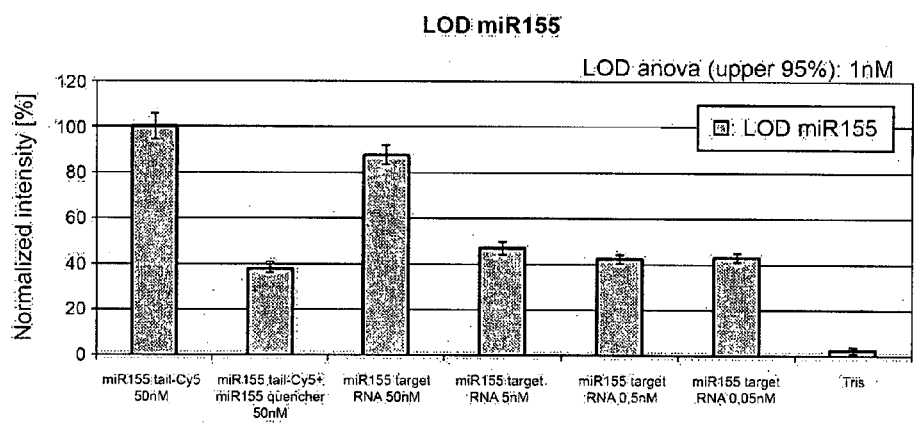
FIG. 5 is a diagram showing the fluorescence recovery as a function of the different concentrations of the target sequence.

As may be noted in FIG. 5, target nucleotide sequences miR155 can be detected up to concentrations of 5 nM with a range from 50 nM to 5 nM and a LOD of 1 nM.

Starting from a concentration of probe 1 and probe 2 of 50 nM, displacement experiments have been carried out using different concentrations of target nucleotide sequences 3 in a range from 50 nM to 0.05 nM. It may be noted that for concentrations below 0.5 nM there are no variations in the fluorescence with respect to the duplex between probe 1-probe 2, so that it is not possible to observe such a variation by means of spectrofluorimetry. In the range from 50 nM to 5 nM there are significant variations in fluorescence. The data of fluorescence emission as a function of the concentration were processed by means of linear regression and the value of limit of detection was extrapolated (LOD=1 nM).

Example 6—Homogeneous Phase Assay with Long Probes

To prove that probe kit 10 according to the invention is capable of capturing and distinguishing target nucleotide sequences 2 even within longer sequences (as would occur in an actual context, since target nucleotide sequence 3 would be within a gene), displacement experiments were carried out using the 99 base long nucleotide sequences shown in table 2. These experiments were carried out in homogeneous phase.

TABLE 2

| Probe name | Sequences | Length (nt) |
|---|---|---|
| HIV 100 R | 5'TGGAATTAGGCCAGTAGTATCAACTCAACTGCTGTTAAATGG CAGTCTAGCAGAAGAAGAGGTAGTAATTAGATCTGTCAATTTCA CGGACAATGCTAA-3' (SEQ ID NO: 19) | 99 |
| HIV 100 M | 5'TACAAATGTCAGCACAGTACAATGTACACATGGAATTAGGCC AGTAGTATCAACTCAACTGCTGTTAAATGGCAGTCTAGCAGAAG AAGAGGTAGTAAT-3' (SEQ ID NO: 20) | 99 |
| HIV 100 L | 5'TAATAAGACGTTCAATGGAACAGGACCATGTACAAATGTCAG CACAGTACAATGTACACATGGAATTAGGCCAGTAGTATCAACTC AACTGCTGTTAAA-3' (SEQ ID NO: 21) | 99 |

The HIV 100 R, HIV 100 M and HIV 100 L probes were designed so that target nucleotide sequence 3 is respectively at the 5' end, in the middle and at the 3' end of the 99 base long sequence.

Figure 6:
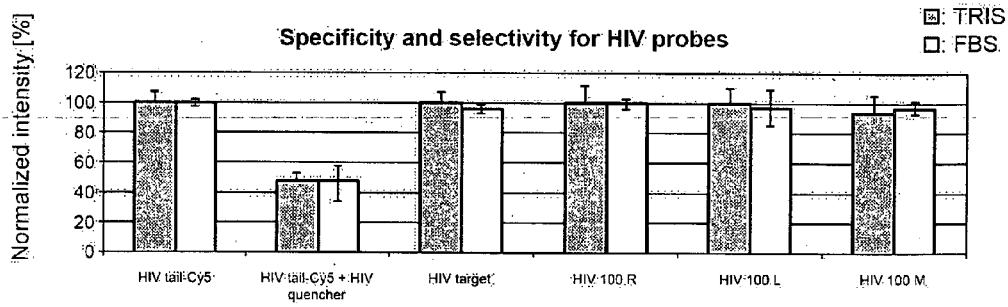
FIG. 6 is a diagram showing the selectivity and the specificity in the formation of the duplex between a second probe of the probe kit of FIG. 1 and a target sequence inserted in longer nucleotide sequences (100 nt)
Figure 10:
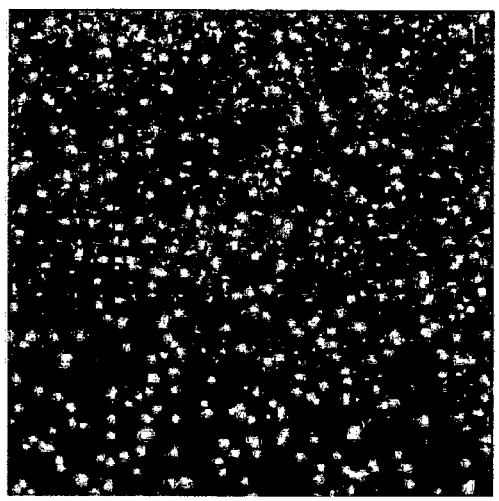
FIG. 10 shows an example of microparticles conjugated with the first probe of the probe kit of FIG. 1 after displacement, on which the analysis of emitted fluorescence is performed.
Figure 11A:
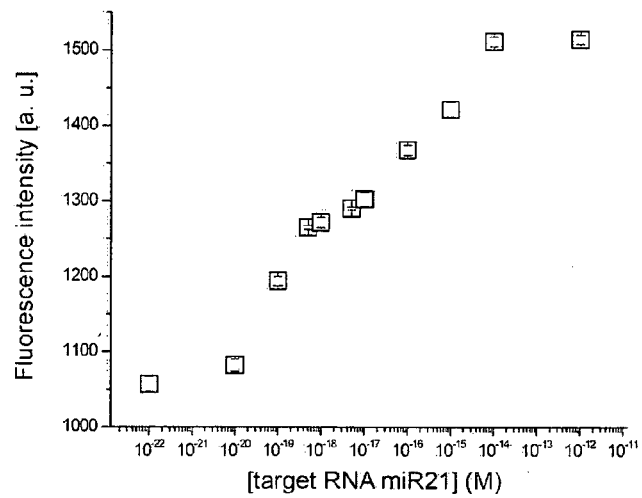
FIG. 11a is a diagram showing the fluorescence recovery on the surface of the microgels as a function of the different concentrations of the target sequence (mir21)
Figure 11B:
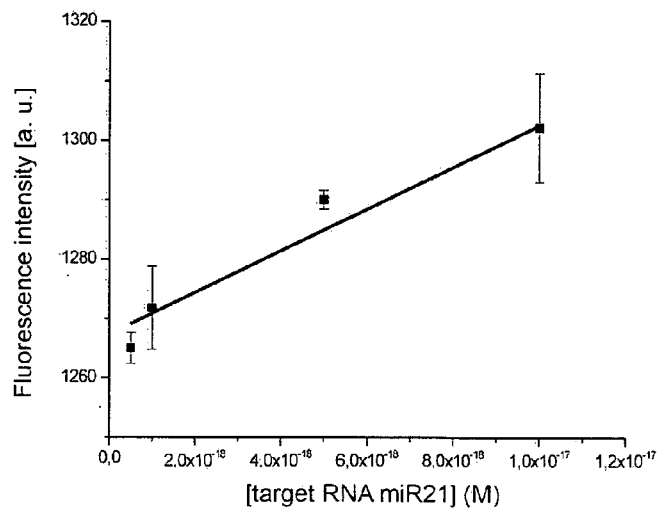
FIG. 11b is a diagram showing the linear regression of the fluorescence emissions as a function of the concentration of the target sequence for the computation of the detection limit (mir21).

The results shown in FIG. 6 prove that the probes are capable of hybridizing and displacing probe 2 in Tris buffer as well as in a complex environment such as that of serum proteins (FBS). With respect to the short 99 base long target sequences, they are recognised without significant statistical differences.

Example 7—Heterogeneous Phase Assay (Microparticle Conjugated Probes)

FIG. 3 diagrammatically shows the heterogeneous phase assay.

Approximately 1 mg of first probe conjugated with the microgel (in 250 µl of Tris HCl hybridization buffer pH 8) was mixed with 350 pmoles of second probe (250 µl). The mixture was incubated at room temperature overnight. The microgels were then washed with hybridization buffer and resuspended in 1 ml of buffer at a final concentration of 1 µg/µl. 50 µl (50 µg) of quenched microgel were mixed to 450 µl of a solution containing target probe sequences 3 at different concentrations ranging from $10^{-11}$ to $10^{-22}$ M and incubated at room temperature overnight. The microgel was precipitated down by centrifugation at 6000 rpm for 15 min at 4° C. The supernatant was removed carefully with a pipette and the precipitant was resuspended in 1 ml of Tris HCl, pH 8 buffer by agitating with a pipette tip and brief vortexing.

30 µl of coupled, quenched and strand displaced microgels were loaded onto µ-slide channels (Ibidi, Martinsried, Del.), illuminated at confocal laser scanning microscope and fluorescence images of microparticles were collected. All captured images were analysed with a public domain image-processing Image J (version 1,43i, NIH, Bethesda, Md.). The image was then further processed with the Analyze Particles function Image J to determine the number of single fluorescence particles computationally. The size of the particles was set to reduce false positive signals generated from noises. For each experiment, at least 200 microparticles were selected for each sample to be analysed.

Example 8—Heterogeneous Assay with HIV-DNA and miRNA21 as Target Nucleotide Sequence Two case studies are hereinafter disclosed to prove the ability of the assay to capture single strand target nucleotide sequences. In particular, an HIV target DNA and an RNA (miRNA 21) were used.

The steps of conjugation of probe 1 with microparticles 4 and of design of probe kit 10 are the same in the two cases. The difference resides only in target nucleotide sequence 3. In the case of the miRNA the formation of a heteroduplex is also shown.

Probes 1 (12 bases) specific for each target nucleotide sequence 3 and functionalised with an amine group at the 3' end were conjugated with the carboxylic groups on the surface of the microgel. Fluorophore 11 bound at the 5' of each probe 1 was Cy5. Respective probes 2 (39 bases) carrying BHQ2 as quencher 23 were hybridized to probe 1.

FIG. 8 shows images acquired by CLSM and the intensities measured along the axis of the microgel. The channel for the analysis of the code and for the detection of the displacement are shown in the lower part.

The close proximity between Cy5 and BHQ2 results in the quenching of the fluorescence of Cy5. Solutions containing target nucleotide sequences 3 (39 bases) were brought in contact with 50 µg of microparticles 4 inducing the hybridisation of each probe 2 with respective target nucleotide sequences 3 and the subsequent emission of fluorescence by Cy5. The emission of Cy5 can be calibrated to evaluate the correspondence between the fluorescence emission (recovery) and the concentration of target nucleotide sequence 3.

FIG. 9A shows the recovery of fluorescence on the surface of microgels as a function of the different concentrations of the target sequence (HIV).

30 µl of coupled, quenched and strand displaced microgels were loaded onto µ-slide channels (Ibidi, Martinsried, Del.), illuminated at confocal laser scanning microscope and fluorescence images of microparticles were collected. All captured images were analysed with a public domain image-processing Image J (version 1,43i, NIH, Bethesda, Md.). The image was then further processed with the Analyze Particles function Image J to determine the number of single fluorescence particles computationally. The size of the particles was set to reduce false positive signals generated from noises or aggregates formation. For each experiment, at least 200 microparticles were selected for each sample to be analysed.

TABLE 3

| ID microparticle | Fluorescence emission |
| --- | --- |
| 1 | 1001 |
| 2 | 1001 |
| 3 | 1002 |
| 4 | 1002 |
| 5 | 1002 |
| 6 | 1003 |
| 7 | 1003 |
| 8 | 1003 |
| 9 | 1003 |
| 10 | 1004 |
| 11 | 1004 |
| 12 | 1004 |
| 13 | 1005 |
| 14 | 1005 |
| 15 | 1006 |
| 16 | 1006 |
| 17 | 1007 |
| 18 | 1007 |
| 19 | 1007 |
| 20 | 1007 |
| 21 | 1007 |
| 22 | 1008 |
| 23 | 1008 |
| 24 | 1009 |
| 25 | 1009 |
| 26 | 1009 |
| 27 | 1010 |
| 28 | 1010 |
| 29 | 1011 |
| 30 | 1011 |
| 31 | 1012 |
| 32 | 1012 |
| 33 | 1012 |
| 34 | 1013 |
| 35 | 1013 |
| 36 | 1014 |
| 37 | 1014 |
| 38 | 1014 |
| 39 | 1014 |
| 40 | 1015 |
| 41 | 1015 |
| 42 | 1015 |
| 43 | 1015 |
| 44 | 1015 |
| 45 | 1016 |
| 46 | 1016 |
| 47 | 1016 |
| 48 | 1016 |
| 49 | 1017 |
| 50 | 1017 |
| 51 | 1018 |
| 52 | 1019 |
| 53 | 1019 |
| 54 | 1019 |
| 55 | 1020 |
| 56 | 1020 |
| 57 | 1020 |
| 58 | 1020 |
| 59 | 1021 |
| 60 | 1022 |
| 61 | 1023 |
| 62 | 1024 |
| 63 | 1024 |
| 64 | 1024 |
| 65 | 1024 |

TABLE 3-continued

| ID microparticle | Fluorescence emission |
|---|---|
| 66 | 1024 |
| 67 | 1024 |
| 68 | 1025 |
| 69 | 1025 |
| 70 | 1025 |
| 71 | 1026 |
| 72 | 1026 |
| 73 | 1026 |
| 74 | 1026 |
| 75 | 1027 |
| 76 | 1027 |
| 77 | 1028 |
| 78 | 1028 |
| 79 | 1029 |
| 80 | 1029 |
| 81 | 1029 |
| 82 | 1030 |
| 83 | 1031 |
| 84 | 1031 |
| 85 | 1031 |
| 86 | 1032 |
| 87 | 1032 |
| 88 | 1032 |
| 89 | 1033 |
| 90 | 1033 |
| 91 | 1033 |
| 92 | 1034 |
| 93 | 1035 |
| 94 | 1036 |
| 95 | 1037 |
| 96 | 1038 |
| 97 | 1038 |
| 98 | 1038 |
| 99 | 1039 |
| 100 | 1040 |
| 101 | 1041 |
| 102 | 1042 |
| 103 | 1042 |
| 104 | 1043 |
| 105 | 1044 |
| 106 | 1044 |
| 107 | 1044 |
| 108 | 1046 |
| 109 | 1047 |
| 110 | 1047 |
| 111 | 1047 |
| 112 | 1048 |
| 113 | 1048 |
| 114 | 1049 |
| 115 | 1049 |
| 116 | 1049 |
| 117 | 1049 |
| 118 | 1049 |
| 119 | 1050 |
| 120 | 1051 |
| 121 | 1051 |
| 122 | 1052 |
| 123 | 1052 |
| 124 | 1053 |
| 125 | 1053 |
| 126 | 1054 |
| 127 | 1055 |
| 128 | 1055 |
| 129 | 1056 |
| 130 | 1056 |
| 131 | 1056 |
| 132 | 1056 |
| 133 | 1057 |
| 134 | 1058 |
| 135 | 1059 |
| 136 | 1059 |
| 137 | 1059 |
| 138 | 1060 |
| 139 | 1060 |
| 140 | 1060 |
| 141 | 1060 |
| 142 | 1060 |
| 143 | 1060 |
| 144 | 1060 |
| 145 | 1061 |
| 146 | 1061 |
| 147 | 1062 |
| 148 | 1062 |
| 149 | 1062 |
| 150 | 1062 |
| 150 | 1062 |
| 151 | 1063 |
| 152 | 1063 |
| 153 | 1064 |
| 154 | 1064 |
| 155 | 1064 |
| 156 | 1064 |
| 157 | 1065 |
| 158 | 1065 |
| 159 | 1066 |
| 160 | 1067 |
| 161 | 1067 |
| 162 | 1067 |
| 163 | 1068 |
| 164 | 1068 |
| 165 | 1068 |
| 166 | 1068 |
| 167 | 1068 |
| 168 | 1068 |
| 169 | 1069 |
| 170 | 1070 |
| 171 | 1070 |
| 172 | 1070 |
| 173 | 1071 |
| 174 | 1072 |
| 175 | 1074 |
| 176 | 1074 |
| 177 | 1075 |
| 178 | 1075 |
| 179 | 1076 |
| 180 | 1077 |
| 181 | 1077 |
| 182 | 1077 |
| 183 | 1079 |
| 184 | 1079 |
| 185 | 1080 |
| 186 | 1080 |
| 187 | 1081 |
| 188 | 1081 |
| 189 | 1082 |
| 190 | 1082 |
| 191 | 1083 |
| 192 | 1083 |
| 193 | 1084 |
| 194 | 1085 |
| 195 | 1086 |
| 196 | 1086 |
| 197 | 1087 |
| 198 | 1087 |
| 199 | 1087 |
| mean ± sd | 1041 ± 25 |

The disclosed kit allows to obtain a linear response in the emission of fluorescence in the range of concentrations between $10^{-17}$ M and $10^{-19}$ M. The graph in FIG. 9*b* shows the linear regression of the fluorescence emissions as a function of the concentration of the target sequence in the range between $10^{-17}$ M and $10^{-19}$ M. The limit of detection (LOD) for HIV has been computed considering the value of fluorescence emission of the background (intercept of the linear regression line) plus 3 times the standard deviation of the value itself (LOD=0.790 aM).

From an analysis of the features of kit 10 for detecting a single-strand target nucleotide sequence 3 according to the present invention, the advantages it allows to obtain are apparent.

In particular, kit 10 allows to detect target nucleotide sequences 3:
  avoiding the separation of the sample and/or the amplification of target nucleotide sequence 3 (leading to a simple, faster and more cost-effective assay),
  with very low concentrations (<1·10$^{-17}$ M) of target nucleotide sequence 3,
  with very short target nucleotide sequences 3 (20-40 nucleotides).

In virtue of the design of probes 1 and 2 by means of very specific parameters, a very high specificity can be obtained, allowing to obtain a very low aspecific signal even when complex samples with several protein species are analysed.

In virtue of the possibility of using a virtually indefinite number of fluorophores and the ever greater availability of fluorophores on the market, the kit according to the invention allows a very high multiplexing.

Kit 10 works in assays for target nucleotide sequences 3 both of DNA and RNA.

Moreover, in virtue of the conjugation on the surface of microparticles 4 of probe 1, a high number of probes 1 can be concentrated in an extremely limited area. This allows to increase the sensitivity of the assay.

The combination between multilayer microparticles 4 and kit 10 allows to:
  obtain a very fast assay (in virtue of a high reaction kinetics),
  assemble and handle multilayer microparticles 4 in miniaturised devices (lab-on-chips).

It is finally clear that modifications and variants which do not depart from the scope of protection defined by the claims may be made to kit 10 for detecting a single strand target nucleotide sequence 3.

The invention claimed is:

1. A kit for detecting a single strand target nucleotide sequence comprising:
    at least one first nucleic acid probe of from 10 to 14 bases, a fluorophore bound to the 5' end thereof, and a micro particle bound covalently to the 3' end of the at least one first nucleic acid probe;
    at least one second nucleic acid probe of from 35 to 50 bases, comprising, from 5' to 3':
        a first segment having a nucleotide sequence complementary to the first nucleic acid probe,
        at least one quencher, and
        a second segment having a nucleotide sequence complementary to at least part of the target nucleotide sequence, wherein the following relation is met:

$|\Delta G$ hybr.target-probe2$| > |\Delta G$ hybr.probe1-probe2$|$, where:
        $\Delta G$ hybr.target-probe2 is the free energy of duplex formation between the target nucleotide sequence and the second nucleic acid probe, and
        $\Delta G$ hybr.probe1-probe2 is the free energy of duplex formation between the first nucleic acid probe and the second nucleic acid probe.

2. The kit according to claim 1 wherein:

10 Kcal/mol $> |\Delta G$ hybr.target-probe2$| - |\Delta G$ hybr.probe1-probe2$| > 50$ Kcal/mol.

3. The kit according to claim 2 wherein the single strand target nucleotide sequence is DNA and 35 Kcal/mol $> |\Delta G$ hybr.target-probe2$| - |\Delta G$ hybr.probe1-probe2$| > 45$ Kcal/mol.

4. The kit according to claim 2 wherein the single strand target nucleotide sequence is miRNA and 10 Kcal/mol $> |\Delta G$ hybr.target-probe2$| - |\Delta G$ hybr.probe1-probe2$| > 25$ Kcal/mol.

5. The kit according to claim 1 wherein the at least one first nucleic acid probe has a length from 11 to 13 bases.

6. The kit according to claim 1 wherein the single strand target nucleotide sequence has a length from 15 to 100 bases.

7. The kit according to claim 6 wherein the single strand target nucleotide sequence has a length from 20 to 40 bases.

8. The kit according to claim 1 wherein the single strand target nucleotide sequence is in a concentration from $1 \cdot 10^{17}$ M to $1 \cdot 10^{-19}$ M.

* * * * *

SEQUENCE LISTING

```
<160> NUMBER OF SEQ ID NOS: 27

<210> SEQ ID NO 1
<211> LENGTH: 12
<212> TYPE: DNA
<213> ORGANISM: Human immunodeficiency virus
<220> FEATURE:
<221> NAME/KEY: source
<222> LOCATION: 1..12
<223> OTHER INFORMATION: /mol_type="DNA"
      /organism="Human immunodeficiency virus"

<400> SEQUENCE: 1
actgctgtta aa                                                          12

<210> SEQ ID NO 2
<211> LENGTH: 39
<212> TYPE: DNA
<213> ORGANISM: Human immunodeficiency virus
<220> FEATURE:
<221> NAME/KEY: source
<222> LOCATION: 1..39
<223> OTHER INFORMATION: /mol_type="DNA"
      /organism="Human immunodeficiency virus"

<400> SEQUENCE: 2
tttaacagca gttgagttga tactactggc ctaattcca                             39

<210> SEQ ID NO 3
<211> LENGTH: 39
<212> TYPE: DNA
<213> ORGANISM: Human immunodeficiency virus
<220> FEATURE:
<221> NAME/KEY: source
<222> LOCATION: 1..39
<223> OTHER INFORMATION: /mol_type="DNA"
      /organism="Human immunodeficiency virus"

<400> SEQUENCE: 3
tggaattagg ccagtagtat caactcaact gctgttaaa                             39

<210> SEQ ID NO 4
<211> LENGTH: 12
<212> TYPE: DNA
<213> ORGANISM: Hepatitis C virus
<220> FEATURE:
<221> NAME/KEY: source
<222> LOCATION: 1..12
<223> OTHER INFORMATION: /mol_type="DNA"
      /organism="Hepatitis C virus"
```

```
<400> SEQUENCE: 4
ttccggtgta ct                                                      12

<210> SEQ ID NO 5
<211> LENGTH: 35
<212> TYPE: DNA
<213> ORGANISM: Hepatitis C virus
<220> FEATURE:
<221> NAME/KEY: source
<222> LOCATION: 1..35
<223> OTHER INFORMATION: /mol_type="DNA"
      /organism="Hepatitis C virus"

<400> SEQUENCE: 5
agtacaccgg aattgccagg acgaccgggt cctttt                            35

<210> SEQ ID NO 6
<211> LENGTH: 35
<212> TYPE: DNA
<213> ORGANISM: Hepatitis C virus
<220> FEATURE:
<221> NAME/KEY: source
<222> LOCATION: 1..35
<223> OTHER INFORMATION: /mol_type="DNA"
      /organism="Hepatitis C virus"

<400> SEQUENCE: 6
aaaggacccg gtcgtcctgg caattccggt gtact                             35

<210> SEQ ID NO 7
<211> LENGTH: 12
<212> TYPE: DNA
<213> ORGANISM: SARS coronavirus
<220> FEATURE:
<221> NAME/KEY: source
<222> LOCATION: 1..12
<223> OTHER INFORMATION: /mol_type="DNA"
      /organism="SARS coronavirus"

<400> SEQUENCE: 7
ggctccagta ta                                                      12

<210> SEQ ID NO 8
<211> LENGTH: 37
<212> TYPE: DNA
<213> ORGANISM: SARS coronavirus
<220> FEATURE:
<221> NAME/KEY: source
<222> LOCATION: 1..37
<223> OTHER INFORMATION: /mol_type="DNA"
      /organism="SARS coronavirus"

<400> SEQUENCE: 8
tatactggag ccattgtcta cctgaacact accgcgt                           37

<210> SEQ ID NO 9
<211> LENGTH: 37
<212> TYPE: DNA
<213> ORGANISM: SARS coronavirus
<220> FEATURE:
<221> NAME/KEY: source
<222> LOCATION: 1..37
<223> OTHER INFORMATION: /mol_type="DNA"
      /organism="SARS coronavirus"

<400> SEQUENCE: 9
acgcggtagt gttcaggtag acaatggctc cagtata                           37
```

```
<210> SEQ ID NO 10
<211> LENGTH: 12
<212> TYPE: DNA
<213> ORGANISM: Homo sapiens
<220> FEATURE:
<221> NAME/KEY: source
<222> LOCATION: 1..12
<223> OTHER INFORMATION: /mol_type="DNA"
      /organism="Homo sapiens"

<400> SEQUENCE: 10
cgtgataggg gt                                                              12

<210> SEQ ID NO 11
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="DNA"
      /organism="Homo sapiens"

<400> SEQUENCE: 11
acccctatca cgattagcat taa                                                  23

<210> SEQ ID NO 12
<211> LENGTH: 8
<212> TYPE: DNA
<213> ORGANISM: Homo sapiens
<220> FEATURE:
<221> NAME/KEY: source
<222> LOCATION: 1..8
<223> OTHER INFORMATION: /mol_type="DNA"
      /organism="Homo sapiens"

<400> SEQUENCE: 12 ataggggt                                                                    8

<210> SEQ ID NO 13
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="DNA"
      /organism="Homo sapiens"

<400> SEQUENCE: 13
acccctatca cgattagcat taa                                                  23

<210> SEQ ID NO 14
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="DNA"
      /organism="Homo sapiens"

<400> SEQUENCE: 14
ttaatgctaa tcgtgatagg ggt                                                  23

<210> SEQ ID NO 15
<211> LENGTH: 23
```

```
<212> TYPE: RNA
<213> ORGANISM: Homo sapiens
<220> FEATURE:
<221> NAME/KEY: source
<222> LOCATION: 1..23
<223> OTHER INFORMATION: /mol_type="RNA"
      /organism="Homo sapiens"

<400> SEQUENCE: 15
uuaaugcuaa ucgugauagg ggu                                            23

<210> SEQ ID NO 16
<211> LENGTH: 12
<212> TYPE: DNA
<213> ORGANISM: Homo sapiens
<220> FEATURE:
<221> NAME/KEY: source
<222> LOCATION: 1..12
<223> OTHER INFORMATION: /mol_type="DNA"
      /organism="Homo sapiens"

<400> SEQUENCE: 16
gactgatgtt ga                                                        12

<210> SEQ ID NO 17
<211> LENGTH: 22
<212> TYPE: DNA
<213> ORGANISM: Homo sapiens
<220> FEATURE:
<221> NAME/KEY: source
<222> LOCATION: 1..22
<223> OTHER INFORMATION: /mol_type="DNA"
      /organism="Homo sapiens"

<400> SEQUENCE: 17
tcaacatcag tctgataagc ta                                             22

<210> SEQ ID NO 18
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="RNA"
      /organism="Homo sapiens"

<400> SEQUENCE: 18
uagcuuauca gacugauguu ga                                             22

<210> SEQ ID NO 19
<211> LENGTH: 99
<212> TYPE: DNA
<213> ORGANISM: Human immunodeficiency virus 1
<220> FEATURE:
<221> NAME/KEY: source
<222> LOCATION: 1..99
<223> OTHER INFORMATION: /mol_type="DNA"
      /organism="Human immunodeficiency virus 1"

<400> SEQUENCE: 19
tggaattagg ccagtagtat caactcaact gctgttaaat ggcagtctag cagaagaaga    60
ggtagtaatt agatctgtca atttcacgga caatgctaa                           99

<210> SEQ ID NO 20
<211> LENGTH: 99
<212> TYPE: DNA
<213> ORGANISM: Human immunodeficiency virus 1
```

```
<220> FEATURE:
<221> NAME/KEY: source
<222> LOCATION: 1..99
<223> OTHER INFORMATION: /mol_type="DNA"
      /organism="Human immunodeficiency virus 1"

<400> SEQUENCE: 20
tacaaatgtc agcacagtac aatgtacaca tggaattagg ccagtagtat caactcaact    60
gctgttaaat ggcagtctag cagaagaaga ggtagtaat                           99

<210> SEQ ID NO 21
<211> LENGTH: 99
<212> TYPE: DNA
<213> ORGANISM: Human immunodeficiency virus 1
<220> FEATURE:
<221> NAME/KEY: source
<222> LOCATION: 1..99
<223> OTHER INFORMATION: /mol_type="DNA"
      /organism="Human immunodeficiency virus 1"

<400> SEQUENCE: 21
taataagacg ttcaatggaa caggaccatg tacaaatgtc agcacagtac aatgtacaca    60
tggaattagg ccagtagtat caactcaact gctgttaaa                           99

<210> SEQ ID NO 22
<211> LENGTH: 39
<212> TYPE: DNA
<213> ORGANISM: Artificial Sequence
<220> FEATURE:
<223> OTHER INFORMATION: HIV probe quencher
<220> FEATURE:
<221> NAME/KEY: modified_base
<222> LOCATION: 12
<223> OTHER INFORMATION: BHQ2 (Black hole quencher)

<400> SEQUENCE: 22
tttaacagca gttgagttga tactactggc ctaattcca                           39

<210> SEQ ID NO 23
<211> LENGTH: 35
<212> TYPE: DNA
<213> ORGANISM: Artificial Sequence
<220> FEATURE:
<223> OTHER INFORMATION: HCV second probe quencher
<220> FEATURE:
<221> NAME/KEY: modified_base
<222> LOCATION: 12
<223> OTHER INFORMATION: BHQ2 (Black hole quencher)

<400> SEQUENCE: 23
agtacaccgg atttgccagg acgaccgggt ccttt                               35

<210> SEQ ID NO 24
<211> LENGTH: 37
<212> TYPE: DNA
<213> ORGANISM: Artificial Sequence
<220> FEATURE:
<223> OTHER INFORMATION: SARS second probe quencher
<220> FEATURE:
<221> NAME/KEY: modified_base
<222> LOCATION: 12
<223> OTHER INFORMATION: BHQ2 (Black hole quencher)

<400> SEQUENCE: 24
tatactggag ctattgtcta cctgaacact accgcgt                             37

<210> SEQ ID NO 25
```

```
<211> LENGTH: 23
<212> TYPE: DNA
<213> ORGANISM: Artificial Sequence
<220> FEATURE:
<223> OTHER INFORMATION: miR155 second probe (quencher 12)
<220> FEATURE:
<221> NAME/KEY: modified_base
<222> LOCATION: 12
<223> OTHER INFORMATION: BHQ2 (Black hole quencher)

<400> SEQUENCE: 25
acccctatca ctattagcat taa                                              23

<210> SEQ ID NO 26
<211> LENGTH: 23
<212> TYPE: DNA
<213> ORGANISM: Artificial Sequence
<220> FEATURE:
<223> OTHER INFORMATION: miR155 second probe (quencher 8)
<220> FEATURE:
<221> NAME/KEY: modified_base
<222> LOCATION: 8, 12
<223> OTHER INFORMATION: BHQ2 (Black hole quencher)

<400> SEQUENCE: 26
acccctatca ctattagcat taa                                              23

<210> SEQ ID NO 27
<211> LENGTH: 22
<212> TYPE: DNA
<213> ORGANISM: Artificial Sequence
<220> FEATURE:
<223> OTHER INFORMATION: miR21 second probe (quencher 12)
<220> FEATURE:
<221> NAME/KEY: modified_base
<222> LOCATION: 12
<223> OTHER INFORMATION: BHQ2 (Black hole quencher)

<400> SEQUENCE: 27
tcaacatcag tttgataagc ta                                               22
```